(12) United States Patent
Weiner et al.

(10) Patent No.: US 11,771,855 B2
(45) Date of Patent: Oct. 3, 2023

(54) METHODS OF TREATING MEDICAL CONDITIONS WITH OXYGEN

(71) Applicants: Brian Charles Weiner, Gainesville, FL (US); Evan Daniel Weiner, Morganville, NJ (US)

(72) Inventors: Brian Charles Weiner, Gainesville, FL (US); Evan Daniel Weiner, Morganville, NJ (US)

( * ) Notice: Subject to any disclaimer, the term of this patent is extended or adjusted under 35 U.S.C. 154(b) by 464 days.

(21) Appl. No.: 15/867,691

(22) Filed: Jan. 10, 2018

(65) Prior Publication Data

US 2019/0015619 A1 Jan. 17, 2019

Related U.S. Application Data

(60) Provisional application No. 62/444,790, filed on Jan. 10, 2017.

(51) Int. Cl.
*A61M 16/00* (2006.01)
*A61M 16/06* (2006.01)
*A61B 5/00* (2006.01)
*A61M 31/00* (2006.01)

(52) U.S. Cl.
CPC .......... *A61M 16/00* (2013.01); *A61B 5/4216* (2013.01); *A61B 5/4255* (2013.01); *A61B 5/4836* (2013.01); *A61M 16/06* (2013.01); *A61M 16/0666* (2013.01); *A61M 31/00* (2013.01); *A61M 2202/0208* (2013.01); *A61M 2210/1064* (2013.01)

(58) Field of Classification Search
CPC .............. A61M 16/0666; A61M 16/06; A61M 2210/1064; A61M 31/00; A61M 2202/0208; A61M 16/10–1005; A61M 2016/1025; A61M 2202/0266; A61M 16/00; A61M 2210/1042; A61M 2210/1053; A61M 2210/1057; A61M 2210/106; A61M 2202/02; A61M 2202/0007; A61M 2202/0014; A61B 5/4836; A61B 5/4255; A61B 5/4216
See application file for complete search history.

(56) References Cited

U.S. PATENT DOCUMENTS 5,586,551 A * 12/1996 Hilliard ................. A61M 11/06
128/200.14
6,443,148 B1 * 9/2002 Rodocker ............. A61G 10/026
128/202.12
7,563,258 B2 * 7/2009 Garabet ................ A61M 31/00
604/514

(Continued)

OTHER PUBLICATIONS

Chudzinski et al, Acute Colonic Pseudoobstruction, Jun. 2015, Clinics in Colon and Rectal Surgery, 28(2): 112-117 (Year: 2015).*

*Primary Examiner* — Colin W Stuart
(74) *Attorney, Agent, or Firm* — Lawrence B. Goodwin; Mandelbaum Barrett PC

(57) ABSTRACT

By manipulating the partial pressures of oxygen and nitrogen in the trapped air in the bowel with 100% non-rebreather mask oxygen, along with supportive therapy, a method will successfully decompress the colon. This is a low morbidity and low cost treatment which can be a useful adjunct in treating ileus and other gastrointestinal diseases in which luminal distension plays a role.

7 Claims, 1 Drawing Sheet

(56) References Cited

U.S. PATENT DOCUMENTS

| | | | |
|---|---|---|---|
| 2003/0219497 A1* | 11/2003 | Otterbein | A61K 33/00 |
| | | | 424/699 |
| 2006/0201504 A1* | 9/2006 | Singhal | A61M 16/00 |
| | | | 128/204.18 |
| 2007/0255165 A1* | 11/2007 | Uesugi | A61B 1/00135 |
| | | | 600/560 |
| 2008/0230072 A1* | 9/2008 | Rollins | A61M 16/06 |
| | | | 128/207.15 |
| 2015/0320791 A1* | 11/2015 | Wager | A61K 9/0043 |
| | | | 424/613 |

* cited by examiner

METHODS OF TREATING MEDICAL CONDITIONS WITH OXYGEN

CROSS-REFERENCE TO RELATED APPLICATIONS

The present application claims priority to U.S. Provisional Patent Application Ser. No. 62/444,790 entitled "METHODS OF TREATING MEDICAL CONDITIONS WITH OXYGEN," filed Jan. 10, 2017, the disclosure of which is incorporated herein by reference in its entirety.

BACKGROUND

Field of the Invention

Embodiments of the present disclosure generally relate to methods of treating medical conditions with oxygen.

Description of Related Art

Acute colonic pseudo-obstruction [ACPO] is the distension of the intestines with accumulated bowel gas due to an acute colonic motility disorder, or ileus. This relatively common clinical problem often complicates other severe medical and surgical illnesses, and may worsen the prognosis. Current medical and surgical treatments are not completely satisfactory.

SUMMARY

Embodiments of the present disclosure generally relate to methods of treating medical conditions with oxygen.

DRAWINGS

Figure 1:
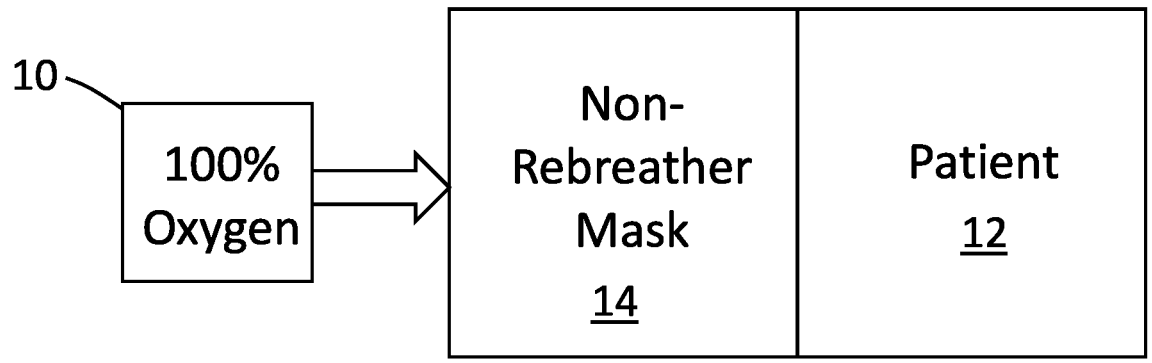
Figure 2:
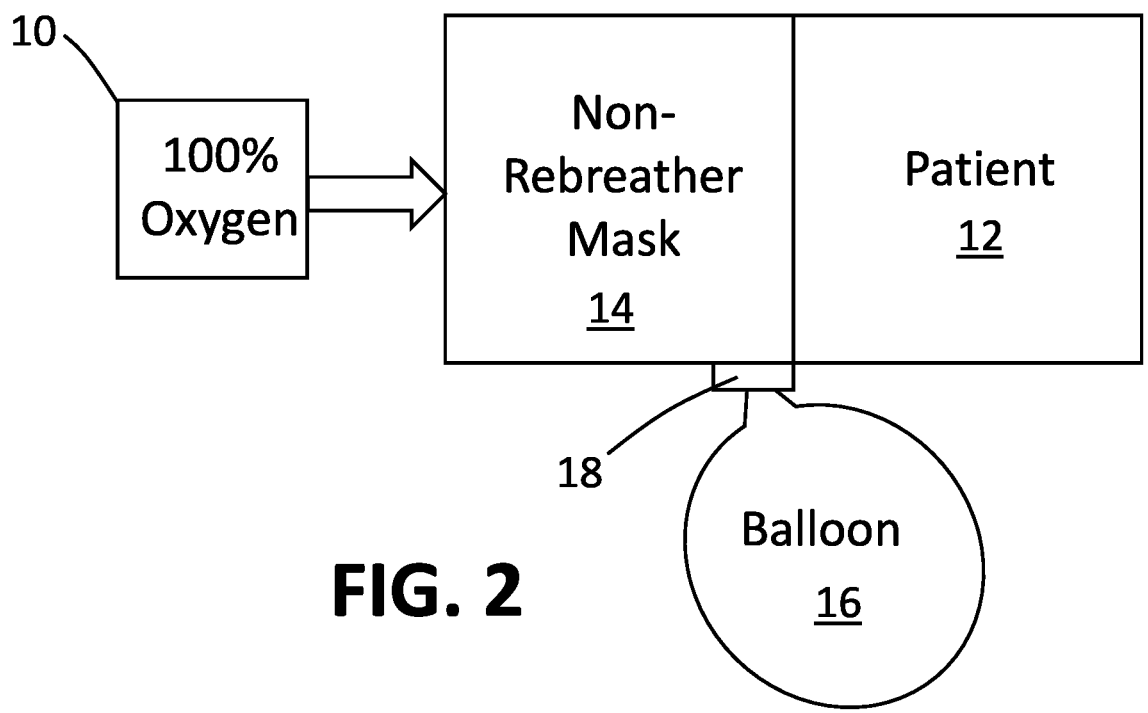

FIG. 1 is an illustration of a source of 100% oxygen, a non-rebreather mask and a patient, for performing the method in accordance with the present invention; and FIG. 2 is an illustration of a source of 100% oxygen, a non-rebreather mask, a patient, and a balloon attached to the mask with a semipermeable membrane in continuity with the oxygen stream for performing a method in accordance with a further aspect of present invention.

DETAILED DESCRIPTION

In the following detailed description, numerous specific details are set forth in order to provide a thorough understanding of exemplary embodiments or other examples described herein. However, it will be understood that these examples may be practiced without the specific details. In other instances, well-known methods and procedures have not been described in detail, so as to not obscure the following description. Further, the examples disclosed herein are for exemplary purposes only and other examples may be employed in lieu of, or in combination with, the examples disclosed. It should also be noted that the examples presented herein should not be construed as limiting of the scope of embodiments of the present invention, as other equally effective examples are possible and likely.

In accordance with a method in accordance with exemplary embodiments, by manipulating the partial pressures of oxygen and nitrogen in the trapped air in the bowel with 100% non-rebreather mask oxygen, along with supportive therapy, this method will successfully decompress the colon. This is a low morbidity and low cost treatment which can be a useful adjunct in treating ileus and other gastrointestinal diseases in which luminal distension plays a role. As shown in FIG. 1, 100% oxygen from source 10 is applied to patient 12 via non-rebreather mask 14.

Acute colonic pseudo-obstruction [ACPO], also known as Ogilvie's syndrome, is a distension of the intestines with accumulated bowel gas due to an acute colonic motility disorder, or ileus. The diagnosis implies the absence of mechanical obstruction. It is most commonly seen after abdominal or pelvic surgery, but can be a complication of surgery at other sites. It may also complicate other gastrointestinal or non-gastrointestinal illnesses. This complication may prolong hospitalization, and lead to delayed wound healing, bowel ischemia and bowel perforation. In a review of hospital records of 106,784 patients with acute colonic pseudo-obstruction, 45.7% had medical complications, 15.9% had procedural complications, and there was a mortality of 7.7%. [1] The diagnosis is suspected clinically by distension of the abdomen and classical obstructive gastrointestinal symptoms of vomiting, nausea, and limited ability to pass flatus. Radiological findings include distended loops of bowel, and a cecum size greater than the normal size of 6 cm. A severe complication of ACPO is distension of the bowel wall to the point of overwhelming wall tension, with resulting ischemia and perforation. This has been observed to be more frequent in cecum diameter of greater than 12 cm. Treatment protocols have been proposed and are directed at decreasing the distension of the colon and restoring normal peristalsis. These include general supportive measures, pharmacologic measures, decompression with nasogastric tube, rectal tube and/or colonoscopy, and surgery. Decompression aims at removing gaseous and liquid contents of the bowel, decreasing distension of the bowel lumen. This would decrease bowel wall tension, allow improved circulation, and work cooperatively with other pharmacologic measures directed at improving peristalsis. Colonoscopy decompression can be provided in refractory cases. Surgery is reserved for the most severe cases or when there is established perforation. With non-surgical treatments, the ileus tends to resolve after 2-6 days. Given the high morbidity and mortality associated with this condition, new medical approaches are much needed to help prevent complications and need for surgery.

In accordance with exemplary embodiments of the present disclosure, the use of high concentration inspired oxygen as a co-therapy for the successful medical management of colonic pseudo-obstruction. While breathing room air at sea level, normal total gas pressure in the end capillary is 706 mmHg. This decrease from atmospheric 760 mmHg is due from a decrease in partial pressure of oxygen from 100 mmHg to 40 mmHg from the arterial to the venous end of the capillaries. However, when a patient breathes 100% oxygen, the total end-capillary gas tension drops to 146.5 mmHg. This is due to the absence of nitrogen, which has a partial pressure of 573 mmHg in the normal capillary alone. The fall in partial pressure of nitrogen in the blood not only prevents the diffusion from the blood into the tissue but also accelerates its diffusion from the tissue into the blood.

In accordance with exemplary embodiments, a pressure gradient in the capillaries of the colonic mesentery produce a similar effect of gas absorption from the colon. The other bowel gas components—nitrogen, carbon dioxide, and methane—can be absorbed as well.

Hyperbaric oxygen therapy has been used for colonic diseases. Pneumotosis intestinalis has been treated with hyperbaric oxygen. More recently, hyperbaric oxygen therapy has been used effectively in post-operative patients at risk of developing a post-operative ileus. As a practical matter, use of hyperbaric oxygen may be awkward to be broadly applied to the systemically ill group of patients afflicted with colonic pseudo-obstruction.

In conclusion, a method of providing periods of high concentrations of inspired oxygen to patients with sufficient lung capacity for gas exchange drives oxygen and other colonic gases from the colon and accelerates the resolution of ileus by decreasing colonic distension and restoring normal mechanical function to the distressed bowel wall.

The above discussion is one possible mechanism of the action of inhaled oxygen. This does not exclude the possibility of alternative mechanisms of action for the purported treatment of gastrointestinal or other medical problems.

It appears that this would also be applicable to patients requiring mechanical respiratory support. It may also be applicable to the management of patients with gastroparesis and small bowel ileus, and even mechanical bowel obstruction.

In accordance with exemplary embodiments, the provision of high concentrations of inspired oxygen become a component of the early adjunctive medical support of all patients with ileus or other gastrointestinal or medical conditions in conjunction with supportive therapy.

High concentrations of inspired oxygen may be useful for a wide variety of medical conditions in which air trapped within a portion of the body may be contributing to the illness. Some examples are: abdominal pain, gastroesophageal reflux disease, peptic ulcer disease, gastroparesis, irritable bowel syndrome, small intestinal bacterial overgrowth, ileus, mechanical obstruction of the bowel, cancers of the gastrointestinal tract, pneumothorax, internal abscess, peritonitis, blunt or sharp trauma including gunshot wound or knife wound. This method may be applicable for other medical illnesses not specified above.

In one configuration, high concentrations of inspired oxygen may be supplemented with other medications, such as carbon monoxide, nitrous oxide or other chemicals miscible or dissolvable in gas/oxygen to enhance the therapeutic effect. In one configuration, perfumes or scented materials may be added to the oxygen to improve palatability to the patient. In another configuration, color may be added to the gas to improve palatability to the patient or to monitor metabolic functions, such as when the gas may turn colors after a specified metabolic event may occur.

In a configuration, a mask appropriate for delivering oxygen to the patient's nose and mouth will be connected to a prefilled oxygen tank, to provide high flow oxygen for a specified period of time, such as a 6-hour time. Smaller oxygen bottles may be provided to allow patients to have greater ease of use.

In a configuration, the mask may have a timer incorporated in it, to measure the amount of time prescribed for use of oxygen.

In a configuration, the mask 14 may be attached to a balloon 16 with the semipermeable membrane 18 in continuity with the high flow oxygen stream from source 10. The membrane 18 may be configured in such a manner as it may mimic the oxygen permeability of the area of the bowel being treated. The balloon 16 may be inflated with air. The semipermeable membrane 18 may allow oxygen exchange and may represent the expected reduction of volume of the portion of bowel in question to which oxygen therapy is directed.

In a configuration, an Oxygen mask may be created that incorporates patient entertainment, such as music, virtual reality, augmented reality materials, to facilitate the patient's comfort during oxygen therapy.

In a configuration, the oxygen mask and the source of portable oxygen may be available as one retail unit, for portable or home use.

In a configuration, medication may be administered to minimize oxygen toxicity. This may be administered to the gas stream itself, enterally, parenterally, transcutaneous, or by other methods that may become available.

It is anticipated that this therapy, which may be provisionally called toga or therapeutic oxygen for gastrointestinal atony, may be assigned a procedure code by the American Medical Association, commonly described as CPT or common procedural terminology. The provision of the CPT code for toga therapy may allow monitoring and payment of licensing fees for this treatment.

This treatment may be used in combination with invasive or noninvasive measurement of oxygen, carbon dioxide or other gases or bodily components, to facilitate proper treatment.

This treatment may be used in conjunction with abdominal imaging such as ultrasonography, routine x-ray/radiology, cross-sectional imaging such as CT scanning or MRI, to enhance the efficacy of the therapy. This treatment may be used in conjunction with measurement of abdominal girth or other measurements of the body to enhance the efficacy of the therapy.

While the foregoing is directed to exemplary embodiments of the present invention, other and further embodiments of the invention may be devised without departing from the basic scope thereof, and should be considered part of this disclosure, as if described fully herein. Specifically, whereas the worldwide web and mobile web are growing content and capabilities at ever-increasing rates, the ability to adapt the systems, methods, applications, and interfaces disclosed herein to existing or new mobile- or web-based technology is contemplated by embodiments of the present invention and does not depart the scope of the invention disclosed herein.

What is claimed is:

1. A method of treating a patient with acute colonic pseudo-obstruction, comprising:
   providing 100% non-rebreather mask oxygen; and
   treating said acute colonic pseudo-obstruction by decompressing said patient's colon by applying said oxygen to said patient, to thereby manipulate partial pressures of oxygen and partial pressures of nitrogen in air trapped in said colon;
   wherein the colon is decompressed and said acute colonic pseudo-obstruction is treated.

2. A method of treating a patient with acute colonic pseudo-obstruction comprising:
   providing a source of 100% oxygen; and
   decompressing said patient's colon by administering said oxygen to said patient, to
   thereby remove gas from said patient's colon and treat said acute colonic pseudo-obstruction.

3. The method of claim 2 further comprising the step of administering said oxygen to said patient through a non-rebreather mask.

4. The method of claim 2 wherein said oxygen is administered to said patient for six hours.

5. The method of claim 2 further comprising the step of supplementing said oxygen with other medications or chemicals miscible or dissolvable in oxygen to enhance said treatment.

6. The method of claim 5 wherein said other medications include one or more of carbon monoxide and nitrous oxide.

7. The method of claim 2 further comprising the step of attaching an air-filled balloon having a semipermeable membrane in continuity with said oxygen, said semipermeable membrane having a permeability mimicking the permeability of the colon, to thereby represent the expected reduction of said gas from said patient's colon.

* * * * *